US00PP26537P3

(12) United States Plant Patent
Caster et al.

(10) Patent No.: US PP26,537 P3
(45) Date of Patent: Mar. 29, 2016

(54) BLUEBERRY PLANT NAMED 'DRISBLUEELEVEN'

(50) Latin Name: ***Vaccinium corymbosum* L.**
Varietal Denomination: DrisBlueEleven

(71) Applicant: DRISCOLL STRAWBERRY ASSOCIATES, INC., Watsonville, CA (US)

(72) Inventors: Brian K. Caster, Salinas, CA (US); Arlen Draper, Payson, AZ (US); Jennifer K. Izzo, Watsonville, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 178 days.

(21) Appl. No.: 13/998,837

(22) Filed: Dec. 13, 2013

(65) Prior Publication Data

US 2015/0173262 P1 Jun. 18, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Jondle & Associates, P.C.

(57) ABSTRACT

A new and distinct variety of blueberry plant named 'DrisBlueEleven' particularly distinguished by having a late harvest season, strong cane renewal and small, firm berries, is disclosed.

2 Drawing Sheets

Genus and species: *Vaccinium corymbosum* L.
Variety denomination: 'DrisBlueEleven'.

BACKGROUND OF THE NEW PLANT

The invention relates to a new and distinct blueberry variety designated 'DrisBlueEleven' and botanically known as *Vaccinium corymbosum* L. This new blueberry variety was discovered in Santa Cruz County, Calif. in September 2001 and originated from a cross between the proprietary female parent blueberry plant 'MS122' (unpatented) and the proprietary male parent blueberry plant 'G455' (unpatented). The original seedling of the new variety was first asexually propagated via softwood cuttings at a nursery in Monterey County, Calif. in 2001. 'DrisBlueEleven' was subsequently asexually propagated via softwood cuttings and underwent further testing at a nursery in Santa Cruz County, Calif. for ten years (2003-2012). The present invention has been found to be stable and reproduce true to type through successive asexual propagations via softwood cuttings.

Plant Breeder's Rights for this variety have not been applied for. 'DrisBlueEleven' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz County, Calif.

1. Late harvest season;
2. Strong cane renewal; and
3. Small, firm berries.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are four years old.

DESCRIPTION OF THE NEW CULTIVAR

Figure 1:
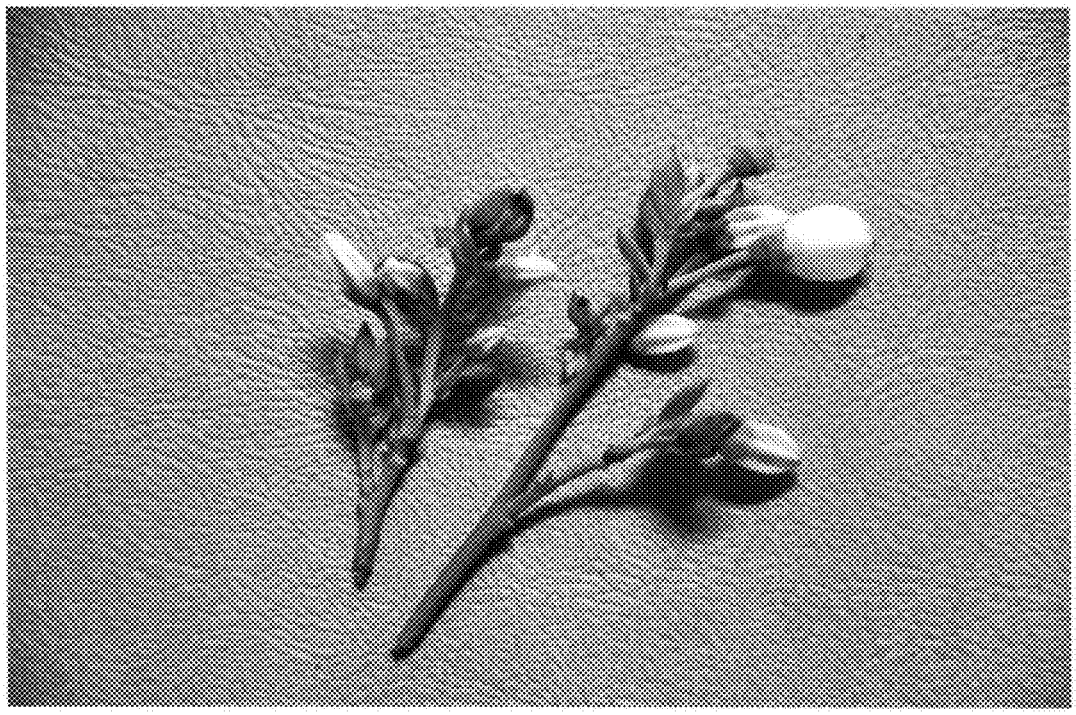
FIG. 1 shows a close-up of flower buds and a mature flower.
Figure 2:
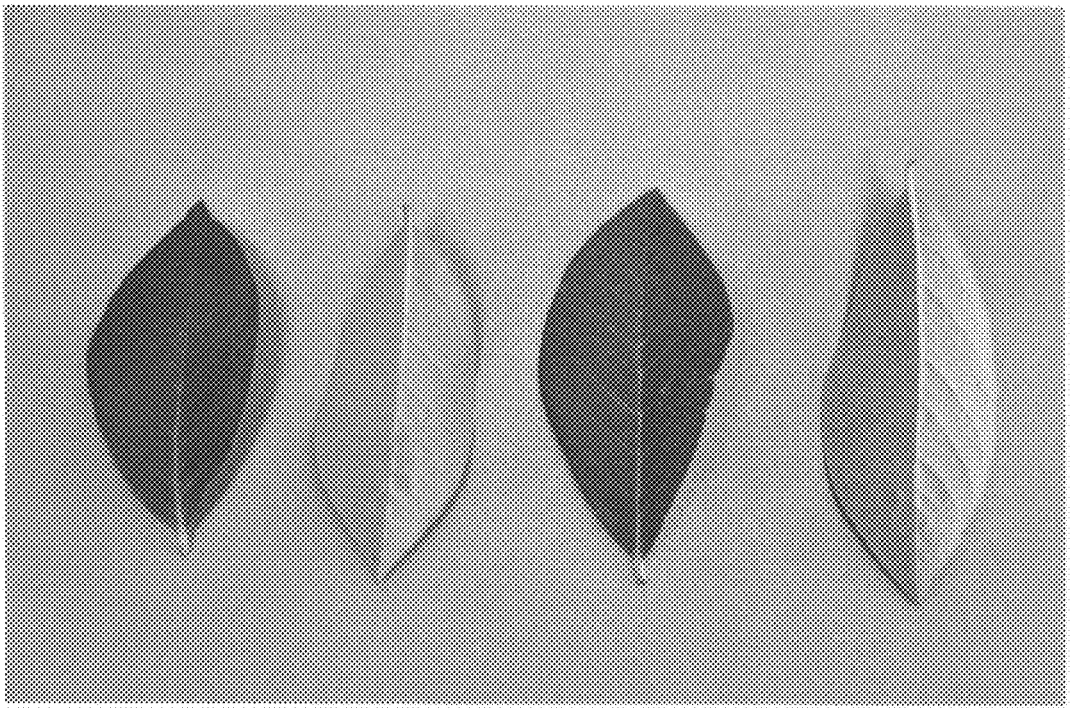
FIG. 2 shows a close-up of the leaves.
Figure 3:
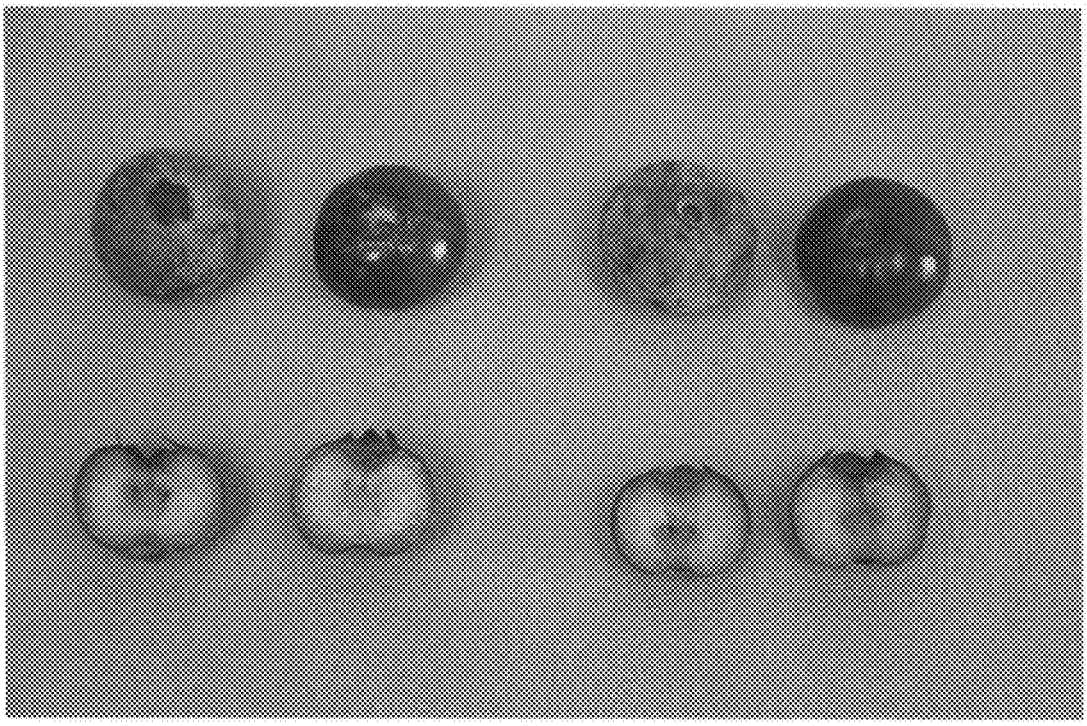
FIG. 3 shows a close-up of the whole fruit and a cross-section of the fruit.

The following detailed description sets forth the distinctive characteristics of 'DrisBlueEleven.' The data which define these characteristics is based on observations taken in Santa Cruz County, Calif. from 2003-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueEleven' has not been observed under all possible environmental conditions. The botanical description of 'DrisBlueEleven' was taken from 4 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueEleven'.

Parentage:

*Female parent.*—The proprietary blueberry plant 'MS122' (unpatented).

*Male parent.*—The proprietary blueberry plant 'G455' (unpatented).

Plant:

*Size.*—Medium.

*Height.*—149.0 cm.

*Width.*—181.4 cm.

*Length/width ratio.*—0.8.

*Plant vigor.*—Medium.

*Growth habit.*—Semi-erect.

*Productivity.*—Medium.

*Cold hardiness.*—Medium; USDA Plant Hardiness Zone 6.

*Chilling requirement.*—High.

*Propagation.*—Soft wood cuttings.

*Time of vegetative bud burst.*—Late.

*Fruiting type.*—Only on one-year-old shoots.

*Cane renewal.*—Strong.

*Internode length* (*upper half on one-year old shoot*).—19.7 mm.

*One-year old canes* (*young canes*).—Length: 32.0 cm. Diameter at the base: 5.0 mm. Diameter at the tip: 2.0 mm. Texture: Smooth. Color (One-year old shoot, branch and canes): RHS 144A (Medium yellow-green).

*Five-year old canes* (*mature canes*).—Length: 130.0 cm. Diameter at the base: 26.0 mm. Diameter at the tip: 2.0 mm. Texture: Rough. Color: RHS 201C (Medium grey).

Leaves:

*Length.*—Medium; 5.79 cm.

*Width.*—Medium; 2.78 cm.

*Length/width ratio.*—2.1; Longer than broad.

*Appearance of leaf bud.*—Medium to late.

*Shape.*—Elliptic.

*Apex.*—Acute.

*Base.*—Cuneate.

*Margin.*—Entire.

*Glossiness.*—Medium.

*Pubescence.*—Glabrous (Absent).

*Sheath.*—Absent.

*Arrangement.*—Alternate.

*Venation.*—Reticulate.

*Color.*—Upper surface: Dark; RHS N137A (Dark green). Lower surface: Light; RHS N138C (Light green).

*Internode length* (*one-year old shoot, upper half*).—Medium; 19.67 mm.

Petiole:

*Length.*—3.0 mm.

*Diameter.*—1.27 mm.

*Color.*—RHS 144C (Medium yellow-green).

Flowers:

*Length* (*excluding peduncle*).—Long; 10.63 mm.

*Diameter.*—7.67 mm.

*Length/width ratio.*—1.4.

*Color.*—RHS 157C (Green-white).

*Flower bud.*—Length: 7.0 mm. Width: 3.0 mm. Number of flowers per bud or peduncle: 4. Anthocyanin coloration: Weak; RHS 64B (Medium red-purple). Color on immature buds: Dark; RHS 184A (Dark greyed-purple). Color on mature buds: Medium; RHS 64A (Medium red-purple).

*Petal width.*—4.24 mm.

*Fragrance.*—Faint.

*Time of beginning flowering on one-year shoot.*—Late.

*Pedicel.*—Length: 4.32 mm. Diameter: 1.16 mm. Color: RHS 142C (Light green).

*Corolla.*—Aperture diameter: 3.13 mm. Shape: Urceolate (Urn-shaped). Size of corolla tube: Medium. Height of corolla tube: 10.63 mm. Diameter of corolla tube: 7.67 mm. Anthocyanin coloration of corolla tube: Present on unopened flowers, not on open flowers; Medium; RHS N57C (Medium red-purple). Ridges on tube: Present.

*Peduncle.*—Length: 11.73 mm. Surface texture: Smooth. Color: RHS 144C (Medium yellow-green).

Reproductive organs:

*Style length* (*including stigma*).—7.96 mm.

*Pollen amount.*—High.

*Pollen color.*—RHS 4D (Light yellow).

*Pollination requirement.*—Intermediate.

*Anther color.*—RHS N172D (Medium greyed-orange).

Fruit:

*Size.*—Small.

*Length.*—10.69 mm.

*Width.*—11.17 mm.

*Length/width ratio.*—1.0.

*Fruit pedicel diameter.*—0.80 mm.

*Weight.*—2.2 g.

*Number of berries per cluster.*—3.70.

*Cluster density.*—Sparse or low.

*Shape in longitudinal sections.*—Round.

*Intensity of green color* (*immature fruit with bloom*).—Medium; RHS 139C (Medium green).

*Color of skin* (*mature fruit without bloom*).—RHS 103A (Dark blue).

*Color of skin* (*mature fruit with bloom*).—RHS 98C (Medium violet-blue).

*Intensity of bloom* (*mature fruit*).—Medium.

*Attitude of sepals.*—Incurving, erect and prostrate.

*Calyx.*—Diameter of basin: Medium; 5.66 mm. Depth of basin: Medium; 4.38 mm. Diameter/depth ratio: 1.3.

*Flesh color.*—RHS 144D (Light yellow-green).

*Firmness.*—Firm.

*Sweetness.*—Low.

*Acidity.*—Medium.

*Time of beginning of fruit ripening* (*one-year old shoots*).—Late.

*Harvest season.*—Late.

*Harvest interval.*—Early June to mid-August.

Seeds:

*Length.*—1.56 mm.

*Width.*—0.98 mm.

*Length/width ratio.*—1.6.

*Abundance.*—Low.

*Color.*—RHS N167A (Medium greyed-orange).

Resistance to pests and diseases: Data not available.

COMPARISON WITH COMMERCIAL VARIETIES

'DrisBlueEleven' differs from the commercial variety 'Elliott' (unpatented) in that 'DrisBlueEleven' has small berries and a late harvest season, whereas 'Elliott' has medium to large sized berries and a very late harvest season.

'DrisBlueEleven' differs from the commercial variety 'Bluecrop' (unpatented), in that 'DrisBlueEleven' has a semi-erect growth habit, whereas 'Bluecrop' has an upright growth habit. Additionally, 'DrisBlueEleven' has small berries, whereas 'Bluecrop' has large berries.

We claim:

1. A new and distinct variety of blueberry plant named 'DrisBlueEleven' as shown and described herein.

* * * * *